US006760923B1

(12) United States Patent
 Tate

(10) Patent No.: US 6,760,923 B1
(45) Date of Patent: Jul. 13, 2004

(54) GLOVE WITH FLEXIBLE JOINTS

(75) Inventor: Albert M. Tate, Austin, TX (US)

(73) Assignee: OriGen Biomedical, Austin, TX (US)

( * ) Notice: Subject to any disclaimer, the term of this patent is extended or adjusted under 35 U.S.C. 154(b) by 0 days.

(21) Appl. No.: 10/361,990

(22) Filed: Feb. 11, 2003

(51) Int. Cl.[7] .............................................. A41D 19/00
(52) U.S. Cl. ............................................. 2/159; 2/163
(58) Field of Search ............................... 2/159, 16, 20, 2/161.1, 161.2, 161.3, 161.4, 161.5, 161.6, 161.7

(56) References Cited

U.S. PATENT DOCUMENTS 2,036,413 A   4/1936 Wendell
4,441,213 A * 4/1984 Trumble et al. ................. 2/16
4,464,796 A   8/1984 Heissenberger et al.
5,323,490 A   6/1994 Yarbrough
5,442,816 A   8/1995 Seketa
5,500,956 A   3/1996 Schulkin et al.

* cited by examiner

Primary Examiner—Gary L. Welch
(74) Attorney, Agent, or Firm—Harrison & Egbert

(57) ABSTRACT

A glove having a body portion of elastomeric material, a plurality of digit portions integrally formed with the body portion and extending outwardly therefrom, and a thumb portion extending outwardly on one edge of the bottom portion. A flexion is formed in the body portion and extends only partially around the root area of the thumb and onto the palm side and the backhand side of the body portion. The flexion is integrally formed with the body portion and has an area projecting outwardly of a surface of a body portion.

17 Claims, 3 Drawing Sheets

GLOVE WITH FLEXIBLE JOINTS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to elastomeric gloves. More particularly, the present invention relates to such elastomeric gloves that have flexible joint portions formed thereon. More particularly, the present invention relates to universal gloves wherein a flexion mechanism is provided so as to facilitate flexing of the digits after application of the gloves.

BACKGROUND OF THE INVENTION

The use of gloves is commonplace in medical and industrial practice in order to protect the user's hands from infectious or irritating agents. These gloves also to help guard against sticking by sharps within the medical environment. Additionally, and furthermore, these gloves are also used for general hygienic purposes. These flexible gloves can be made of latex, vinyl, nitrile, or other elastomeric material. These gloves are often intended for single use in order to prevent contamination.

Disposable gloves are generally available in two (2) types. One is an inexpensive, bulk-packaged "universal" glove in which one glove can fit either hand. Such universal gloves are typically loose fitting in order to accommodate the unique position of the thumb on each hand. As a result, they fit relatively poorly on either hand. Another common type of disposable glove is the "dedicated" glove. This glove is used for surgery or precision work in which the glove must to fit specifically only the right or the left hand. This is a design that results in a generally tight, well-fitting glove.

Dedicated gloves, although better fitting, are more expensive to manufacture than bulk-packaged universal gloves. Dedicated gloves are dip molded on specially designed right or left formers. This results in a glove fitting only the right or left hand. The gloves must be paired in special packaging. This makes such gloves more expensive to purchase. An additional disadvantage of dedicated gloves is that an entire package of a new pair of gloves must be opened in order replace only a single glove if one glove is damaged or lost.

The relatively inexpensive bulk-packaged universal gloves are made on a single former that is designed to fit either hand fairly well. The ability to form the gloves on a single former makes the gloves less expensive to manufacture, package, purchase, and use. The single former used to manufacture universal gloves has the thumb generally in the same plane as the palm of the hand so that the thumb will fit either hand roughly equally. However, in the human hand, the position of a relaxed thumb will drop below the palm rather than being in the same plane as the palm. In use, the elastomer of gloves made on a universal former pulls the thumb rearward, out of its relaxed position, toward the plane of the palm. Constant exertion of the thumb muscles pulling against the elastomer glove are required in order to grasp objects or manipulate tools. This can quickly resulting in fatigue of the thumb. Although less of a problem, hand fatigue of the fingers can also occur from stretching the glove in order to bend the fingers. Since most health care users must change their gloves many times each day, and must wear gloves nearly all day, fatigue and the cost of the gloves are both considerable problems.

Fatigue and discomfort are not merely undesirable, but could be dangerous to the patient or the health care worker wearing the gloves. Distraction, loss of grip or thumb fatigue can result in a mistake, shaky hands, an inadvertent stick with a sharp (such as a needle), or some other undesirable results. The inadvertent transmission of an infectious agent, for example, could result from a needle stick caused by untimely fatigue that results from ill-fitting gloves.

Dedicated gloves are more comfortable to wear and are less likely to cause fatigue than universal gloves. This is due, in part, to the fact that dedicated gloves are made to custom fit either the right or left hand while in a relaxed position. As a result, less stretching of the elastomer is required. Unfortunately, dedicated gloves must be individually packed in pairs. This will increasing the cost of purchase significantly. Dedicated gloves can even be available in different styles in order to optimize fit. This also adds to the cost of the gloves.

In the past various U.S. Patents have issued relating to formed gloves that allow for finger flexibility. For example, U.S. Pat. No. 2,036,413, issued on Apr. 7, 1936 to W. Herbruck, describes the shaping of formed gloves. This patent utilizes various bending grooves formed in the elastic material of the glove in general proximity to the joints of the wearer. Although the gloves of this patent add increased flexibility to the digit portions and thumb portion of the elastic glove, it is not particularly related to universal gloves which must be designed to fit both hands.

U.S. Pat. No. 4,464,796, issued on Aug. 14, 1984 to Heissenberger et al., teaches a glove formed of rubber or plastic material that has a roll-down beaded edge and contains a structured surface at the cuff region. The structured surface is formed at the outer side or surface of the glove by non-connected raised portions. The structured surface is formed at the inside or inner surface of the glove by mirror-image non-connected recess or depressions.

U.S. Pat. No. 5,323,490 issued on Jun. 28, 1994 to D. Yarbrough, teaches a glove having stress relief areas. In particular, the stress relief areas are located adjacent to the individual joints of the hand, fingers and thumb. These stress relief areas provide additional glove material, such as by ribs or bellows formed of peaks and valleys, which reduce the energy expended to overcome the resistance of the material and, thereby, reduce fatigue. Each of these stress relief areas extends entirely around the particular joint. Additionally, each of the stress relief areas does have sharp peaks and valleys which makes manufacture of the glove more difficult.

U.S. Pat. No. 5,500,956, issued on Mar. 26, 1996 to Schulkin et al., describes a basketball glove which has a plurality of protruding elements formed across the palm surface of the glove. The finger elements are each open so as to allow individual fingers of the user to extend there through. An elastic material is formed on the backhand side of the glove so as to provide flexibility to the user.

U.S. Pat. No. 5,442,816, issued on Aug. 22, 1995 to N. F. Seketa, describes a surgical glove with flexible elements formed at the various joints of the glove. These flexible elements are identified as "flextubules" which can be a bell-shaped curve located on the palmar surface of the glove. An accordion fold and a flextuble are located at each of the joints and extend entirely therearound so as facilitate the movement of the various joints placed within the glove.

Each of these prior art patent describes a particular type of dedicated glove. They are not directed toward universal gloves whereby the thumb portion is placed directly between the plane associated with the palm surface of the glove and the plane associated with the backhand surface of the glove. In none of the cases identified in these prior art patents could the construction be utilized in association with the universal glove. None of the flexible portions identified in these gloves is particularly useful for allowing the glove to be adapted to either hand.

It is an object of the present invention to provide a universal glove that is more easily adapted for use on either hand.

It is another object of the present invention to provide a universal glove that facilitates the flexibility of the digit portions and thumb portion of the universal glove.

It is a further object of the present invention to provide a universal glove that provides effective protection to the hands of the user.

It is a further object of the present invention to provide a universal glove that flexes more easily than otherwise allowed by the elastomeric material of the glove.

It is a further object of the present invention to provide a universal glove which enhances the comfort of wearing the glove and reduces the fatigue associated with the use of such glove.

It is still a further object of the present invention to provide a universal glove that can be easily manufactured, simply packaged, and be of minimal cost.

It is still a further object of the present invention to provide a universal glove that will not tear when stripped off of the former or when placed on the hand by the user.

It is a further object of the present invention to provide a universal glove that can be inexpensively manufactured on a universal former.

It is an additional advantage to provide a glove that can be easily placed on the hand and will stay in place on the hand.

These and other objects and advantages of the present invention will become apparent from a reading of the attached specification and appended claims.

BRIEF SUMMARY OF THE INVENTION

The present invention is a universal glove that comprises a body portion formed of elastomeric material, a plurality of digit portions integrally formed with the body portion and extending outwardly therefrom, a thumb portion extending outwardly on one edge of the body portion and integrally formed with the body portion, and a flexion extending only partially around the root area of the thumb and extending onto the palm side and the backhand side of the body portion. The body portion has an opening at the bottom thereof. The plurality of digit portions are in spaced relationship to each other. A flexion is integrally formed with the body portion and has an area projecting outwardly from a surface of the body portion.

In the present invention, the thumb portion has a bottom adjacent to the opening of the body portion. The flexion is interrupted adjacent to the bottom of this thumb portion. The flexion is interrupted on the palm side and the backhand side of the body portion at the bottom of the thumb portion. The flexion is of an inverted U-shaped cross-section.

The thumb portion has a top adjacent to the plurality of digit portions. The flexion can have a width at the top of the thumb portion that is greater than the width of the flexion at a bottom of the thumb portion. The thumb portion extends from the body portion and a plane extending between the palm side and the backhand side of the body portion. The flexion is curved so as to have a concavity facing this thumb portion.

In the present invention, a first knuckle blister is integrally formed on the body portion adjacent to and below the plurality of digit portions. This first knuckle blister is formed on the palm side of the body portion and projects outwardly of the surface of the body portion. A second knuckle blister is integrally formed on the body portion adjacent to and below the plurality of digit portions on the back hand side of the body portion. This second knuckle blister projects outwardly of the surface from the body portion. The present invention can have bilateral symmetry. Each of the knuckle blisters can have a width at a center of the body portion that is greater than a width of the knuckle blister adjacent to the edges of the body portion.

DETAILED DESCRIPTION OF THE INVENTION

Figure 1:
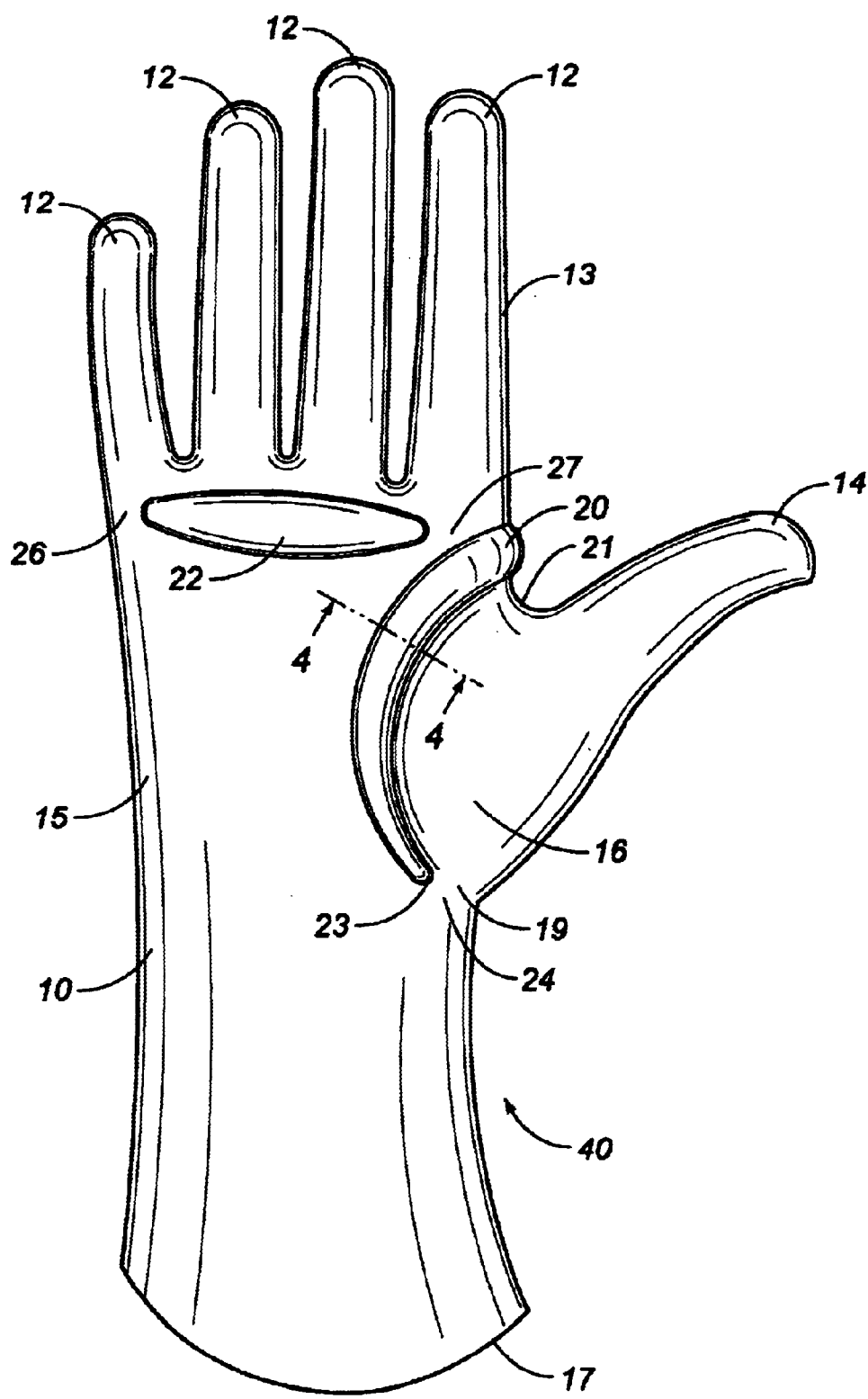
FIG. 1 is plan view showing the palm side of the universal glove of the present invention.

Refeffing to FIG. 1, there is shown the glove 40 in accordance with the teaching of the preferred embodiment of the present invention. Glove 40 includes a body portion 10, digit portions 12 and a thumb portion 14. The digit portions 12 and the thumb portion 14 are integrally formed with the body portion 10. FIG. 1 particularly shows the palm side of the glove 40. The glove 40 also has a first side edge 13 and a second side edge 15. The thumb portion 14 will project outwardly from the first side edge 13. The glove 40 also has a bottom opening 17 so as to allow a human hand to enter the interior of the glove 40. The glove 40 is integrally and unitarily formed together of any elastomeric material, such as rubber, latex, vinyl and/or nitrile.

Figure 2:
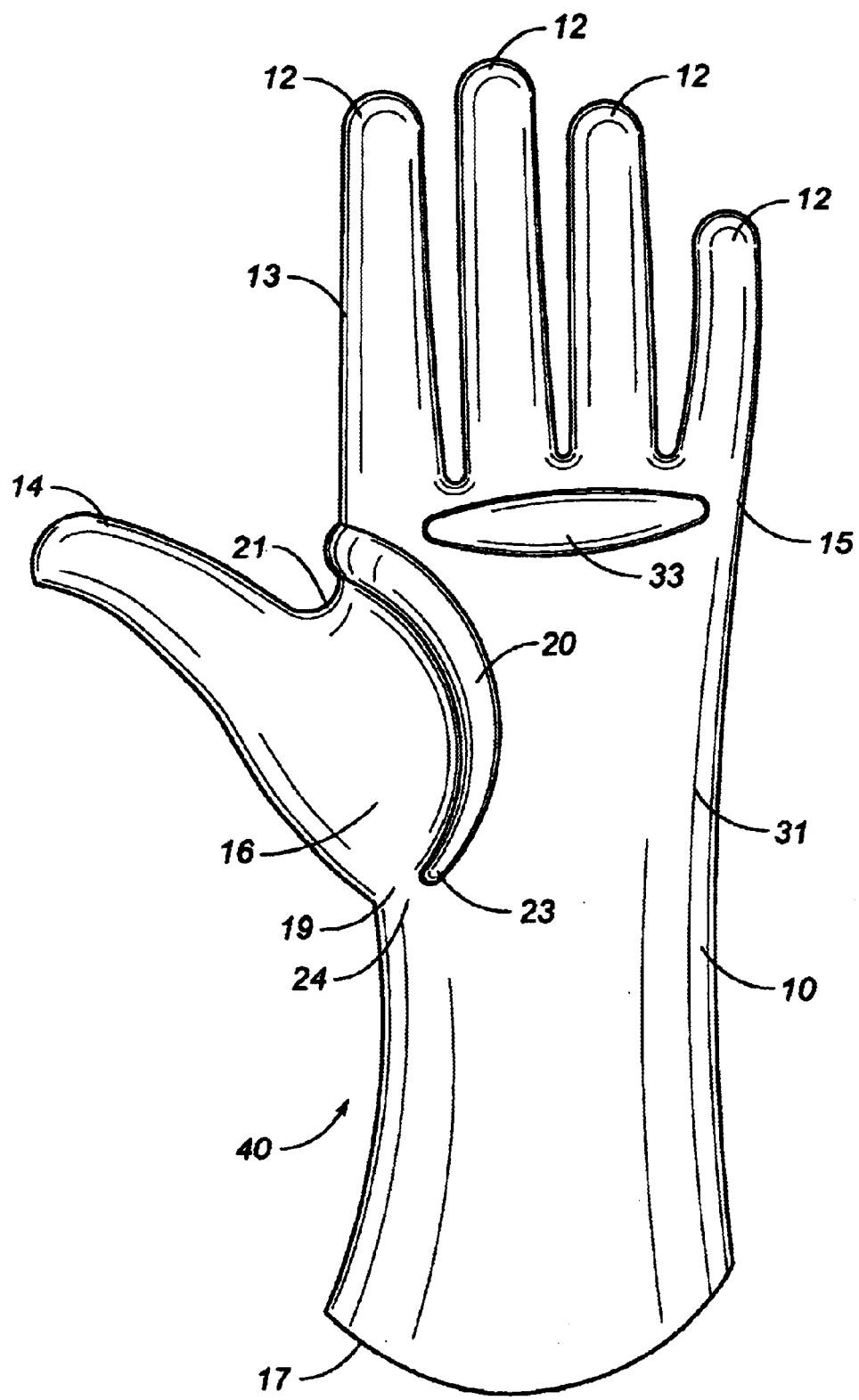
FIG. 2 is a plan view showing the backhand side of the universal glove of the present invention.

Importantly, as can be seen in FIG. 1, the present invention includes a flexion 20 that is formed in the body portion 10 of the glove 40 adjacent to the thumb portion 14. In particular, the flexion 20 is a slightly raised area that extends above the surface of the palm side of the glove 40. The flexion 20 will extend only partially around the thumb portion 14 and is interrupted in an area 19 adjacent to the bottom of thumb portion 14. The flexion 20 will continuously extend around the top 21 of the thumb portion 14 so as to present a mirror image on the back hand side of the glove 40 (as shown in FIG. 2). The flexion 20 has a smaller width at end 23 than at the area adjacent to the top 21 of thumb portion 14. The flexion 20 is formed adjacent to the root area 16 of thumb portion 14 and has a curvature with a concavity facing the thumb portion 14. The flexion 20 provides accordion-like action in response to movement of the thumb within the thumb portion 14 so that when the thumb moves, the flexion 20 compresses on the side of the directions of movement and is pulled flat on the side opposite the direction of movement. As a result, very little effort is required to maintain a human thumb within the glove 40 in a natural resting position (a few centimeters below the palm). The interrupted area 24 is flush with the surface of the body portion 10. As a result, the flexion 20 does not completely encircle the root area 16 of thumb portion 14. Flat area 24 is contiguous with body portion 10 and does not contain any slack material. As such, it is more resistant to stretching than is the flexion 20. The flat area 24 helps to keep thumb portion 14 of glove 40 from creeping off the thumb of the wearer's hand when the glove is put on and used.

A knuckle blister 22 is formed on the body portion 10 of glove 40 generally below the digit portions 12. The knuckle blister 22 is a flexion formed in the upper area of the body portion 10. The knuckle blister 22 has a wide area adjacent to the center of the body portion 10 and tapers so as to narrow in width toward the sides 13 and 15 of the glove 40. A discontinuous area 26 is formed adjacent to the edge 15. Similarly, another discontinuous area 27 is formed adjacent to the edge 13. As such, the knuckle blister 22 does not encircle the body portion 10.

The knuckle blister 22 and the flexion 20 enhance the comfort of wearing the glove 40 and reduce the fatigue associated with the use of the glove 40. The knuckle blister 22 and the flexion 20 may be used in any combination on the glove 40 to enhance fit and comfort to the wearer. It should be noted that the knuckle blister 22 and flexion 20 are mirrored on the opposite side of the glove, as shown in FIG. 2. With this arrangement, the glove may be worn comfortably on either hand. Since the knuckle blister is interrupted by flat area 26 and flat area 27, the knuckle blister 22 does not encircle the plurality of digit portions 12. The flat areas 26 and 27 keep the digit portions of glove 40 from creeping off of the wearer's finger when the glove is put on and used.

Both the knuckle blister 22 and flexion 20 are formed of gently undulating shapes, avoiding sharp peaks and valleys. Such gentle undulation simplifies manufacture and use of the glove and prevents any thin area during manufacture that can be subject to tearing during the use of the glove.

Figure 4:
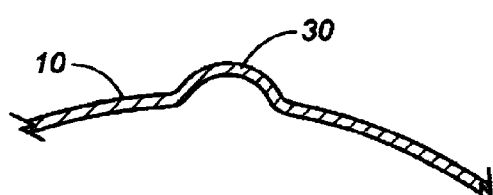
FIG. 4 is a cross-sectional view of the flexion as taken across lines 4—4 of FIG. 1.

As can be seen in FIG. 4, the flexion 20 has a generally inverted U-shaped configuration. The flexion 20 has the same thickness as the remainder of the body portion 10. It is not necessary to create accordion shapes, folds, or other configurations so as to achieve the requisite flexibility associated with the flexion 20. During the manufacture of the flexion 20, a simple ridge can be added to the former so as to allow for the creation of the flexion 20 in a simple and inexpensive manner.

FIG. 2 shows the backhand side 31 of the glove 40. The backhand side 31 also includes body portion 10, the plurality of digit portions 12, the thumb portion 14 and the flexion 20. The backhand side 31 of glove 40 has a second knuckle blister 33 formed adjacent to the plurality of digit portions 12. The knuckle blister 33 has an identical configuration to that of the knuckle blister 22 formed on the palm side of glove 40.

Importantly, in FIG. 2, it can be seen that the flexion 20 extends over the top 21 of the thumb portion 14 and curves along the body portion 10 toward the flat area 24. As such, the flexion 20 extends only partially around the root area 16 of the thumb portion 14. The flexion 20 is discontinuous in the flat area 24 at the bottom 19 of thumb portion 14.

Figure 3:
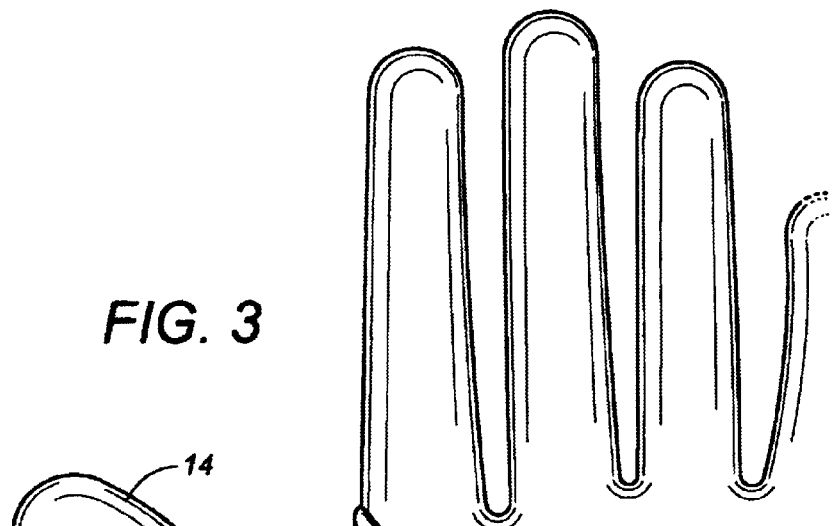
FIG. 3 shows an alternative embodiment of the flexion as used with the thumb portion of the present invention.

FIG. 3 shows an alternative embodiment of the flexion as used in the present invention. In FIG. 3, flexion 30 is made of a plurality of raised portions 32 formed in the body portion 42 of the glove 46. In this embodiment, the shape of the raised portions 32 of flexion 30 is such that slack material in the raised portions 32 may be taken up to compensate for tension in both the X and Y axes. In such a pattern, the raised portions 32 of flexion 30 may be independent or linked with an array of linking raised portions 32. Importantly, in FIG. 3, it can be seen that the flexion 30 is also discontinuous in the area at the bottom 19 of thumb portion 14 in the same manner that the flexion 20 is discontinuous in such area.

In the present invention, the flexion can be pleated, blistered, or bubbled or other waves shaped so as to provide a means that flex the thumb and fingers without pulling against the material of the glove. For the thumb, the flexion 20 allows the thumb to rest in its natural position slightly below the palm of the hand without the wearer having to exert their thumb against the elastomeric material of the glove 40. The shape of the flexion 20 allows the glove material to flex in any direction with very little exertion of energy. The pleats, blisters or waves of the flexion 20 are pulled straight before the particular digit has to work against the elastomeric material of the glove. The human thumb, within the glove 40, can assume a natural resting position, without exerting any significant force against the glove material.

As stated earlier, the prior art gloves do describe flexion areas having narrow peaks and valleys which completely encircle the digit. The consequence of this is that the flexion will stretch during donning and use. This will make the glove very difficult to put on and to keep in place. Since the flexion of the prior art stretch during use the digit portions of the glove will tend to creep down along the digits so as to become baggy and ill-fitting. With the respect to the prior art, it should also be noted that with dip molding, the elastomer material flows off of the peaks and into the valleys so as to create a very thin layer of material at the peak. This very thin area is likely to rip when the glove is put on or even when it is striped off of the former.

The present invention, by providing a wider flexion of an interrupted or discontinuous shape, particularly at the bottom of the thumb portion provides slack material only in the portion of the glove where it is needed. This allows the rest of the glove, including the palm surface and the digits, to enjoy a snug, constant and comfortable fit. The flexions are comprised of undulation with no sharp peaks or valleys. As a result, the present invention avoids the formation of thin spots during the manufacturing of the glove. Also, as a result, the universal gloves in association with the present invention are less likely to be subject to ripping. The former that is used to make the universal glove of the present invention will likewise employ gentle changes of shape. This results in a finished glove which is easier to strip from the former and less likely to tear during manufacture or use. The present invention will result in lower manufacturing costs and few customer complaints.

During use, using the thumb digit as an example, the wearer will put on the glove normally and push his or her own thumb into the glove thumb. The formed flexion shape will leave a slack area at the interdigital cleft and along only a portion of the thumb root. The resulting slack area provides a region of the glove where the thumb or finger movement is first taken up by pulling the slack out of the flexion before the elastomer material will exert a pulling force against the thumb or finger. In contrast, the currently available bulk-packaged gloves necessarily provide too much excess slack to accommodate the movement of the thumb. This results in an ill-fitting glove.

In the present invention, since the thumb body fits closely against the thumb, and since the interruption of the flexion will hold the digit portion in a proper position, tactile feel and gripability are not lost as with the floppy, loose fitting, bulk-packaged gloves or those gloves with encircling flexions. The flexion of the present invention allows the thumb to work efficiently and without fatigue, while the area where the flexion is interrupted will keep the thumb or digit portion in its proper place.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A glove comprising:
   a body portion comprised of an elastomeric material, said body portion having a palm side and a backhand sides, said body portion having an opening at a bottom thereof;
   a plurality of digit portions integrally formed with said body portion and extending outwardly therefrom, said plurality of digit portions being in spaced relationship to each other; and
   a thumb portion extending outwardly on one edge of said body portion, said thumb portion having a root area contiguous with said body portion, said thumb portion being integrally formed with said body portion, said body portion having a flexion extending only partially around said root area of said thumb and extending onto to said palm side and said backhand side of said body portion, said flexion being integrally formed with said body portion and having an area projecting outwardly of a surface of said body portion, said thumb portion having a top adjacent said plurality of digit portions, said flexion having a width at said top of said thumb portion that is greater than a width of said flexion at a bottom of said thumb portion.

2. The glove of claim 1, said thumb portion having a bottom adjacent said opening of said body portion, said flexion being interrupted adjacent to said bottom of said thumb portion.

3. The glove of claim 2, said flexion being interrupted on said palm side and said backhand side of said body portion at said bottom of said thumb portion.

4. The glove of claim 1, said flexion having an inverted U-shaped cross-section.

5. The glove of claim 1, said thumb portion extending from said body portion in a plane extending between said palm side and said backhand side of said body portion.

6. The glove of claim 1, said flexion being curved so as to have a concavity facing said thumb portion.

7. The glove of claim 1, further comprising:
   a knuckle blister integrally formed on said body portion adjacent to and below said plurality of digit portions, said knuckle blister formed on said back hand side of said body portion, said knuckle blister projecting outwardly of the surface of said body portion.

8. A glove comprising:
   a body portion comprised of an elastomeric material, said body portion having a palm side and a backhand sides, said body portion having an opening at a bottom thereof;
   a plurality of digit portions integrally formed with said body portion and extending outwardly therefrom, said plurality of digit portions being in spaced relationship to each other;
   a thumb portion extending outwardly on one edge of said body portion, said thumb portion having a root area contiguous with said body portion, said thumb portion being integrally formed with said body portion, said body portion having a flexion extending only partially around said root area of said thumb and extending onto to said palm side and said backhand side of said body portion, said flexion being integrally formed with said body portion and having an area projecting outwardly of a surface of said body portion; and
   a knuckle blister integrally formed on said body portion adjacent to and below said plurality of digit portions, said knuckle blister formed on said palm side of said body portion, said knuckle blister projecting outwardly of the surface of said body portion.

9. The glove of claim 8, further comprising:
   a second knuckle blister integrally formed on said body portion adjacent to and below said plurality of digit portions, said second knuckle blister formed on said backhand side of said body portion opposite in location to said knuckle blister formed on said palm side of said body portion, said second knuckle blister projecting outwardly of said surface of said body portion, said knuckle blisters being unconnected to each other at a first edge and a second edge of said body portion between said palm side and backhand side.

10. The glove of claim 9, each of said knuckle blisters having a width at a center of said body portion that is greater than a width of the knuckle blister adjacent said first and second edges.

11. The glove of claim 8, said elastomeric material selected from the group consisting of rubber, latex, vinyl and nitrile.

12. A glove comprising:
    a body portion formed of an elastomeric material, said body portion having a palm side and a backhand side;
    a plurality of digit portions integrally formed with said body portion and extending outwardly therefrom, said plurality of digit portions being in spaced relationship to each other; and
    a thumb portion extending outwardly on one edge of said body portion, said body portion having a flexion formed therein and extending adjacent to said body portion around said palm side and said backhand side of said body portion, said flexion being discontinuous on said body portion adjacent a bottom of said thumb portion, said flexion being curved so as to have a concavity facing said thumb portion, said flexion integrally formed with said body portion and projecting outwardly of a surface of said body portion, said thumb portion having a top adjacent said plurality of digit portions, said flexion having a width at a top of said thumb portion that is greater than a width of said flexion at said bottom of said thumb portion.

13. The glove of claim 12, the discontinuity of said flexion having a portion on said palm side and a portion on said backhand side.

14. The glove of claim 12, said flexion having an inverted U-shaped cross-section.

15. The glove of claim 12, said thumb portion extending from said body portion in a plane extending between said palm side and said backhand side of said body portion.

16. A glove comprising:
    a body portion formed of an elastomeric material, said body portion having a palm side and a backhand side;

a plurality of digit portions integrally formed with said body portion and extending outwardly therefrom, said plurality of digit portions being in spaced relationship to each other;

a thumb portion extending outwardly on one edge of said body portion, said body portion having a flexion formed therein and extending adjacent to said body portion around said palm side and said backhand side of said body portion, said flexion being discontinuous on said body portion adjacent a bottom of said thumb portion, said flexion being curved so as to have a concavity facing said thumb portion, said flexion integrally formed with said body portion and projecting outwardly of a surface of said body portion;

a first knuckle blister integrally formed on said body portion adjacent to and below said plurality of digit portions, said first knuckle blister formed on said palm side of said body portion, said first knuckle blister projecting outwardly of the surface of said body portion; and a second knuckle blister integrally formed on said body portion adjacent to and below said plurality of digit portions, said second knuckle blister formed on said backhand side of said body portion, said second knuckle blister projecting outwardly of the surface of said body portion.

17. The glove of claim 16, each of said first and second knuckle blisters having a width at a center of said body portion that is greater than a width of the knuckle blister extending outwardly from the center of said body portion.

\* \* \* \* \*